(12) United States Patent  
Head et al.

(10) Patent No.: US 9,187,687 B2
(45) Date of Patent: Nov. 17, 2015

(54) METHODS FOR INCREASING METHANOGENESIS IN SUBSURFACE RESERVOIRS

(75) Inventors: Ian McCutcheon Head, Calgary (CA); Stephen Richard Larter, Calgary (CA); Ian Donald Gates, Calgary (CA)

(73) Assignee: PROFERO ENERGY INC., Calgary, AB (CA)

( * ) Notice: Subject to any disclaimer, the term of this patent is extended or adjusted under 35 U.S.C. 154(b) by 563 days.

(21) Appl. No.: 13/515,774

(22) PCT Filed: Dec. 29, 2010

(86) PCT No.: PCT/GB2010/052212
§ 371 (c)(1),
(2), (4) Date: Oct. 3, 2012

(87) PCT Pub. No.: WO2011/080518
PCT Pub. Date: Jul. 7, 2011

(65) Prior Publication Data
US 2013/0020073 A1  Jan. 24, 2013

Related U.S. Application Data

(60) Provisional application No. 61/291,753, filed on Dec. 31, 2009.

(51) Int. Cl.
*E21B 43/22* (2006.01)
*C12P 5/02* (2006.01)
(Continued)

(52) U.S. Cl.
CPC . *C09K 8/582* (2013.01); *C12N 1/38* (2013.01); *C12P 5/023* (2013.01); *Y02E 50/343* (2013.01)

(58) Field of Classification Search
CPC ......... C12P 5/023; C09K 8/582; E21B 43/16; E21B 43/006; E21B 43/25; E21B 43/295
See application file for complete search history.

(56) References Cited

U.S. PATENT DOCUMENTS 3,332,487 A   7/1967  Jones
7,832,475 B2  11/2010  Jin et al.
(Continued)

FOREIGN PATENT DOCUMENTS

CA      2638451      2/2010
WO   WO 01/68904 A1   9/2001
(Continued)

OTHER PUBLICATIONS

International Search Report for PCT Patent Application No. PCT/GB2012/052215 (filed Dec. 29, 2010).
(Continued)

*Primary Examiner* — Zakiya W Bates
(74) *Attorney, Agent, or Firm* — Foley & Lardner LLP (57) ABSTRACT

Methods for increasing the increasing the rate of methane production in a subsurface reservoir are provided, for example by identifying the petroleum components in the reservoir; identification of microbes and nutrients contained in the formation water; selection of additional nutrients shown to be effective for the particular microbial consortium in that reservoir and then enhancing and preferably maximizing the total amount of nutrients available to the microbes in a manner such that methane generation is maximized while at the same time ensuring that the concentration of nutrients in the well is non-lethal to the microbes.

26 Claims, 3 Drawing Sheets

(51) Int. Cl.
*C09K 8/582* (2006.01)
*C12N 1/38* (2006.01)

(56) References Cited

U.S. PATENT DOCUMENTS

| | | |
|---|---|---|
| 2001/0045279 A1 | 11/2001 | Converse et al. |
| 2005/0115649 A1 | 6/2005 | Tokarz et al. |
| 2007/0295505 A1 | 12/2007 | Pfeiffer |
| 2010/0101782 A1 | 4/2010 | Pfeiffer et al. |
| 2010/0190203 A1 | 7/2010 | Pfeiffer et al. |
| 2011/0250582 A1 | 10/2011 | Gates et al. |
| 2011/0284215 A1 | 11/2011 | Pfeiffer et al. |

FOREIGN PATENT DOCUMENTS

| | | |
|---|---|---|
| WO | WO 2005/115649 A1 | 12/2005 |
| WO | WO-2010/012093 | 2/2010 |

OTHER PUBLICATIONS

PCT International Search Report and Written Opinion dated Mar. 7, 2013 in related PCT Patent Application No. PCT/CA2012/000642.

METHODS FOR INCREASING METHANOGENESIS IN SUBSURFACE RESERVOIRS

CROSS-REFERENCE TO RELATED APPLICATIONS

This application is the U.S. national stage application of International Patent Application No. PCT/GB2010/052215, filed on Dec. 29, 2010, which claims priority to U.S. Ser. No. 61/291,753, filed on Dec. 31, 2009, each of which is incorporated herein by reference in its entirety.

BACKGROUND OF THE INVENTION

Subsurface oil reservoirs are promising and important sources for the generation and collection of increasing amounts of methane gas as an energy source. In particular, since at best about 40% of oil is recoverable from oil reservoirs, methods for the conversion of the remaining oil in the reservoirs to clean fuels such as methane are of great interest. Microbes are responsible for biodegrading conventional crude oil to intermediates that are converted by other microbes (methanogens) into methane leaving behind heavy oil, which can be then further biodegraded. The processes of heavy oil formation and methane gas generation (methanogenesis) occur over geological time scales of millions of years. Microbial conversion of oil to methane involves a variety of multi-step pathways and a consortium of microorganisms working together in concert. Pathways include fermentation of oil to acetate, $CO_2$ and hydrogen, as well as microbial oxidation of acetate to $CO_2$ and hydrogen and subsequent microbial reduction of $CO_2$ to methane with hydrogen. Other pathways include direct fermentation of acetate to methane. Each of these biochemical transformations are carried out by specific types of microbes and often take place in the face of competing reactions such as conversion of methane and the acetate and hydrogen intermediates to other products such as $H_2S$, $H_2O$, and $CO_2$.

It has been recognized that the naturally slow methanogenic biodegradation process can be accelerated to enhance methane production in the reservoir. For example, as described in WO 2005/115649 entitled "Process for Stimulating Production of Methane from Petroleum in Subterranean Formations", techniques are described for injecting one or more agents into a reservoir in which methanogenic microbial consortia are present to modify the reservoir environment to promote in situ microbial degradation of petroleum, promote microbial generation of methane, and to demote in situ microbial degradation of methane.

While that reference describes generic procedures for enhanced methane production, there is still a need for improved methods for stimulating methane production to maximize the potential of subsurface oil reservoirs as sources of methane. Adding the proper amounts and types of agents and nutrients to optimally stimulate methane production from the particular petroleum components found in an oil reservoir remains a considerable challenge in view of the variety of microbes and pathways involved, including microbes that may be present in the reservoir but that do not participate or are deleterious to methane production. For example, stimulation and the growth of non-methanogens may out-compete methanogens for common intermediates essential to methane production or drive microbial transformations to products (e.g. $CO_2$, $H_2S$, etc.) other than methane.

BRIEF SUMMARY OF THE INVENTION

This invention is based, in part, on the discovery that significant enhancement in methane generation from oil reservoirs can be achieved. In one aspect, such enhancement can be effected by identifying the petroleum components in the reservoir; identification of and nutrients contained in the formation water; selection of additional nutrients shown to be effective for the particular microbial consortium in that reservoir and then enhancing and preferably maximizing the total amount of nutrients available to the microbes in a manner such that methane generation is maximized while at the same time ensuring that the concentration of nutrients in the well is non-lethal to the microbes.

That is to say that there are several independent variables regarding enhanced methanogenesis all of which require careful analysis. These include but are not limited to:

Identification of the particular petroleum components in the reservoir and determining if these components are amenable to methanogenesis;

Determining what methanogenic microbial consortia are present;

Analyzing the formation water in the reservoir and then determining the total amount of nutrient to be added at a well head to enhance the rate of methanogenesis so as to provide for commercially viable amounts of methane production at the well head. In a preferred embodiment, commercially viable rates of methanogenesis from the reservoir include an incremental increase in methane production levels at the well head of at least 20 MCF per day;

Adding the nutrients to the reservoir in a manner that does not significantly alter the bulk salinity and make-up of the formation water while at the same time allowing rapid dispersion of the nutrients into as much of the formation water as possible.

Determining the maximum concentration of nutrient in the well such that the nutrient concentration is non-lethal to the methanogenic microbial consortia but enhances methanogenesis as per above. As to this latter variable, consideration must be given to the amount of nutrients already in the reservoir such that the total nutrient concentration does not exceed the lethal concentration.

In a preferred embodiment, the methane production levels at the well head are increased incrementally by at least 25 MCF and preferably at least 50 MCF per day.

In view of the above, in one of its embodiments, this invention is directed to a method for enhancing methanogenesis in an oil reservoir which method comprises:

a) identifying a reservoir comprising petroleum components suitable for methanogenesis, formation water and methanogenic microbial consortia wherein said reservoir is endogenously producing a first rate of methane as measured in MCF methane production at a well head per day of less than 0.02 MCF;

b) identifying a set of nutrients based on the formation water and endogenous microbes present in the reservoir wherein said nutrients are selected from the group of endogenous nutrients already in the formation water and/or exogenous nutrients which are not present in the formation water;

c) adding a first solution comprising methanogenenic nutrients based on the identification set forth in b) above wherein said nutrients comprise at least nitrogen and phosphate ions and further wherein the amount of the nutrients in the first solution is sufficient to enhance the rate of methanogenesis in said reservoir at its final dilution without being lethal to said methanogenic microbial consortia and further wherein the concentration of nutrients in said solution added facilitates dispersion of the nutrients from the first solution into the formation water;

d) maintaining the reservoir under conditions so as to produce a second rate of methane production at the well head of at least 0.7 MCF methane per day.

Preferably, the second rate of methane production at the well head is at least 7 MCF methane per day.

The solution of nutrients is preferably an aqueous solution and can occur in a single injection or in an iterative process where the aqueous solution is divided into several injections wherein each injection contains a know concentration of nutrients. After each injection, the concentration of nutrients in the formation water is determined and adjustments are made to each additional injection to achieve the desired concentration of nutrients in the formation water.

In a preferred embodiment, the amount of water used to inject the nutrients is minimized such that the injected water does not significantly alter the composition of the formation water but for the nutrients added. That is to say that the salinity of the formation water will not vary by more than 1% and preferably not more than 0.1% after injection as compared to prior to injection except for changes in concentration of the nutrients added. Examples of characteristics which are not significantly altered include salinity, pH, temperature, non-nutrient ion concentrations, etc.

When limited amounts of water are employed, this translates into higher concentrations of nutrients in the water to be injected. Upon injection, these higher concentrations facilitate dispersion and diffusion of the nutrients into the formation water away from the injection site. In one preferred embodiment, the concentration of each nutrient added to the aqueous solution is at least 2% of its saturation concentration but always below any lethal level for the microorganisms.

The term "saturation concentration" refers to either the concentration of the nutrient itself or as a complex with a sequestering agent as is well known in the art.

Still further, maintaining the reservoir under conditions wherein methane production at the well head is at least 0.7 MCF per day can include periodic measurement of the nutrient levels in the formation water and adding additional nutrients as necessary.

In another embodiment, there is provided a method for increasing the rate of methanogenesis in a petroleum reservoir which method comprises:

a) evaluating the petroleum components in the reservoir, methanogenic microbial consortia present, stimulants and/or inhibitors already present in the reservoir, pressure and temperature, and salinity of formation water in the reservoir;

b) evaluating the nature and amount of stimulants and/or inhibitors to be added based on the evaluation in a) above wherein said stimulants and/or inhibitors are selected from the group of endogenous and/or exogenous stimulants and/or inhibitors;

c) injecting through a well head a solution of stimulants to the reservoir in an amount such that their concentration in the reservoir is above the critical concentration to effect enhanced methanogenesis but below a lethal dosing to the methanogenic microbial consortia; and d) maintaining said reservoir under conditions such that the rate of methanogenesis is increased to the point that methane production at the well head is at least a 20 MCF incremental increase in methane production at the well head per day prior to the injection of the solution.

Preferably, the incremental increase in methane production at the well head is at least 40 MCF and more preferably at least 50 MCF.

Preferably, the solution is an aqueous solution.

In an optional embodiment, a second solution can be injected into the reservoir through the well head to enhance methanogenesis. Such a second solution comprises an inhibitor or mixture of inhibitors wherein the amount of the inhibitors in the second solution is sufficient to maintain a rate of methanogenesis in said reservoir in conjunction with the added nutrients such that the methane production at the well head is at least a 20 MCF incremental increase in methane per day and wherein the amount of inhibitors added to said reservoir water is non-lethal to said microbes.

In one embodiment, the inhibitors are included in an aqueous solution and, in another embodiment, the inhibitors are combined with the solution of stimulants. In another embodiment, the inhibitors are included in a separate aqueous solution from that of the stimulants.

In still another embodiment, there is provided a method for increasing the rate of methanogenesis in a reservoir which method comprises:

a) evaluating petroleum components in the reservoir, methanogenic microbial consortia present, stimulants and/or inhibitors already present in the reservoir, pressure and temperature, and salinity of formation water in the reservoir;

b) confirming the presence of at least one or more of the microbes that comprise a methanogenic consortium selected from the group consisting of members of the Methanomicrobiales (*Methanocalculus* spp., *Methanogenium* spp., *Methanoculleus* spp.), the Methanosarcinales and anaerobic hydrocarbon fermenting bacteria such as *Syntrophus* spp., *Smithella* spp., *Syntrophobacter* spp., *Syntrophomonas* spp., and *Marinobacter* spp.;

c) evaluating the nature and amount of stimulants to be added based on the evaluation in a) and b) above wherein the stimulants are selected from the group consisting of those that stimulate one or more members of the methanogenic microbial consortium set forth in b) and further wherein said stimulants are either endogenous and/or exogenous stimulants;

d) evaluating the nature and amount of optional inhibitors to be added based on the evaluation in a) and b) above wherein the inhibitors are selected from the group consisting of those that inhibit one or more non-methanogenic pathways and further wherein said inhibitors are either endogenous and/or exogenous inhibitors;

e) injecting a solution of stimulants into the reservoir through a well head such that after injection the total concentration in the reservoir of stimulants is above the critical concentration to effect enhanced methanogenesis but below a lethal dosing for the methanogenic microbial consortia set forth in b) above wherein the amount of solution employed facilitates dispersion of the nutrients from the aqueous solution into the formation water;

f) optionally injecting a solution comprising inhibitors into the reservoir through the well head such that after injection the total concentration in the reservoir of inhibitors is above the critical concentration to effect inhibition of non-methane producing competing reactions but below a lethal dosing for the methanogenic microbes set forth in b) above wherein the amount of solution employed facilitates dispersion of the nutrients into the formation water; and g) maintaining said reservoir under conditions such that the rate of methanogenesis is increased to the point that methane production at a well head is at least a 20 MCF incremental increase in methane generation at the well head per day prior to the injection of the solution of nutrients and the optional solution of inhibitors.

In still another embodiment of the methods of this invention, the stimulants comprise at least ammonium ($NH_4^+$) and phosphate ($PO_4^{3-}$) ions, or components that generate these in situ and wherein the ammonium ion concentration preferably ranges from 500-800 ppm. This and other aspects of the invention are further described in the text that follows.

DETAILED DESCRIPTION OF THE INVENTION

In this specification and in the claims that follow, reference will be made to a number of terms that shall be defined to have the following meanings unless specified otherwise:

DEFINITIONS

As used in the specification and claims, the singular form "a", "an" and "the" include plural references unless the context clearly dictates otherwise.

As used herein, the term "comprising" is intended to mean that the compositions and methods include the recited elements, but not excluding others.

As used herein, the term "about" when used in association with a measurement, or used to modify a value, a unit, a constant, or a range of values, refers to variations of +/−3%. It is to be understood, although not always explicitly stated that all numerical designations are preceded by the term "about". Accordingly all numerical designations, e.g., pH, temperature, time, concentration, and molecular weight, including ranges, are approximations which are varied (+) or (−) by increments of 3%. It also is to be understood, although not always explicitly stated, that the reagents described herein are merely exemplary and that equivalents of such are known in the art.

The term "ppm" or "parts per million" as used herein refers to the mass ratio of solutes to water multiplied by one million. 1 ppm is equivalent to 1 mg/L.

The term "methanogenic microbes" refers to those microbes or combination of microbes that produce methane from oil in hydrocarbon reservoirs. Such microbes are anaerobic and, accordingly, exogenous oxygen is contra-indicated during any injection. Methanogenic microbes are well known in the art and include, by way of example only, *Methanocalculus* spp., *Methanogenium* spp., *Methanoculleus* spp., members of the Methanosarcinales (all methanogenic archea), and associated syntrophic organisms providing acetate and hydrogen for the methanogens these including *Syntrophus* spp., *Smithella* spp. *Marinobacter* spp., *Syntrophobacter* spp., *Syntrophomonas* spp. (all syntrophic bacterial partners that may convert hydrocarbons to substrates for methanogenic archaea) and the like.

The term "non-lethal" means that after addition of the stimulant solution and optionally the inhibitor solution, a viable population of methanogenic microbes remain in the formation water.

The term "nutrient" or "methanogenic nutrient" (sometimes referred to herein as "stimulant") refers to a component or mixture of components such as gases, inorganic or organic ions including anions, cations and combinations thereof (salts) which facilitate growth of one or more methanogenic microbes. To facilitate growth, the nutrients can supply one or more key nutritional components to one or more of the microbes comprising the consortium of methanogenic microbes.

The nutrient can be either an endogenous nutrient already present in the formation water or an exogenous nutrient—one which is not present in the formation water.

In one embodiment, the nutrient is an inorganic salt and more preferably is an inorganic salt selected from one or more of $NH_4Cl$, $KH_2PO_4$, $FeSO_4.7H_2O$, $MnCl_2.4H_2O$, $CoCl_2.6H_2O$, $NiCl_2.6H_2O$, $CuCl_2.2H_2O$, $ZnSO_4.7H_2O$, $Na_2MoO_4.H_2O$, $Na_2SeO_3.5H_2O$, $Na_2WO_4.2H_2O$, POx compounds were x is 2, 3 or 4, $Na_3PO_4$, $K_3PO_4$, $KH_2PO_4$, $K_2HPO_4$, $NaH_2PO_4$, $Na_2HPO_4$, $H_3PO_4$, $H_3PO_3$, $H_3PO_2$, $C_1$-$C_{20}$ alkyl phosphate compounds, $(C_1$-$C_{20})_3$trialkyl phosphate such as triethyl phosphate), tripoly phosphates, condensed forms of phosphoric acid, including tripolyphosphoric acid, pyrophosphoric acid, salts of condensed phosphoric acids, e.g., potassium or sodium tripolyphosphate, and the like. Both hydrated and anhydrous forms may be used.

Components heretofore considered as nutrients have been found to deleterious to methanogenesis and in a preferred embodiment are excluded from the nutrient composition. Such components include sulfate, nitrate, nitrite, and oxygen.

The term "inhibitor" refers to a component or mixture of components such as inorganic or organic compounds including anions, cations and combinations thereof (salts) which inhibit one or more microbial reactions which either degrade methane and/or inhibit one or more reactions which divert the petroleum components in the reservoir into products other than methane ("competing reactions"). Such inhibitors can be components that interfere with one or more of these competing reactions or which are selectively toxic to non-methanogenic microbes. Preferably, such inhibitors are one or more components that interfere with such competing reactions. In a preferred embodiment, the inhibitor is an inorganic salt and more preferably is a molybdate salt such as sodium molybdate ($Na_2MoO_4$), and hydrates thereof which are inhibitors of sulfate reducers, and sodium chlorate ($NaClO_3$) for inhibiting nitrate reducers.

The inhibitor can be either an endogenous inhibitor—one which is already present in the formation water or an exogenous inhibitor—one which is not present in the formation water.

The term "non-nutrient" refers to components which are not nutrients or inhibitors. Such non-nutrients include sodium chloride and other salts which affect the salinity of the water in the reservoir. In general, the microbes are adapted to the salinity of the formation water. The injection strategy seeks to maintain essentially the same gross salinity of the formation water after injection as was present prior to injection.

The term "petroleum components suitable for methanogenesis" refers to liquid, gaseous or solid hydrocarbons (hydrocarbon only) or related petroleum non-hydrocarbons (those containing hydrogen and carbon plus one or more heteroatoms such as sulphur, nitrogen or oxygen) all of which are the major biodegradable components of oil. Preferred oils are those rich in n-alkanes in reservoirs in the carbon number range 3 to 30 where natural biodegradation is occurring. Typically, n-alkanes represent up to a maximum around 10 weight percent of the petroleum components and typically petroleum/oils suitable for methanogenesis will have from 1-5% n-alkanes present. Especially preferred oils will also contain an extended suite of homologous alkylbenzenes and alkyltoluenes. Oil viscosity can range from very low values (from 5 or 10 centipoise (cP) at 20° C.) to values as high as 7000 cP at reservoir conditions. Low values generally mean more reactive oils but higher values favor gas over oil production. While n-alkane rich oils are preferred the inventors have shown that in many reservoirs oils without n-alkanes or alkybenzenes acceleration of natural methanogenesis is possible as the microorganisms have adapted to consumption of less desirable reactants.

"Formation water" refers to the water endogenously present in the reservoir and includes the cations, anions, soluble organics, and other components as well as its temperature, pH, salinity, etc.

"MCF" means one thousand (1,000) cubic feet.

"Incremental increase in methane per day" refers to the increase in methane production when the reservoir has been treated under conditions to stimulate methanogenesis and is measured when the rate of methanogenesis (as determined by the amount of methane produced per day at the well head) is at least 80% of the maximum rate of methane generated from the reservoir over a 60 day period and preferably over a 120 day period.

"Well head" refers generically to any well head in the reservoir. Reference to a single well head is not intended herein as injection of stimulants and/or inhibitors can be conducted at a first well head and the methane produced by enhanced methanogenesis can be captured at the same or different well head in the reservoir.

Methodology

This invention is predicated on the discovery that prior failed attempts to reach commercial rates of methane production via enhancing in situ methanogenesis were based on the inability to properly correlate all factors involved in methane production. This invention is further predicated on the discovery that once a sufficient number of factors affecting methanogenesis are properly addressed by e.g., adjusting the amount and type of nutrients, etc., and then injecting such nutrients into the reservoir under appropriate conditions, enhanced methanogenesis at commercially viable rates can be achieved.

Figure 1:
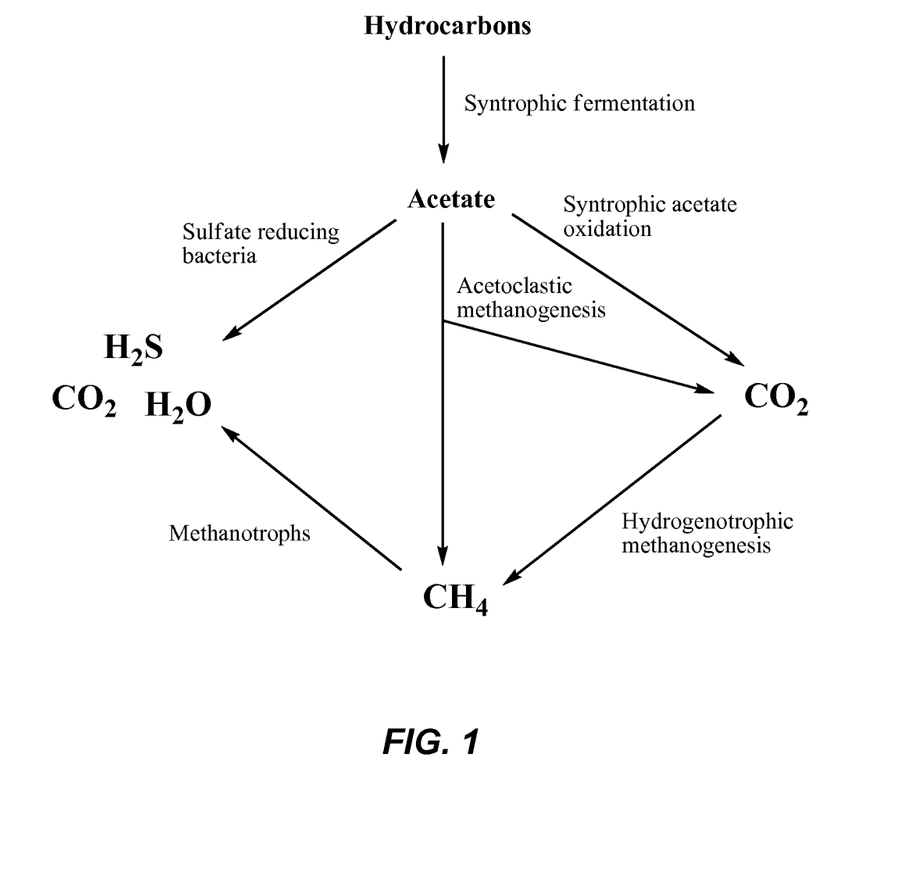
FIG. 1 shows the various microbial mediated pathways that convert hydrocarbons to methane via an acetate intermediate. Also shown are pathways that degrade methane and acetate.

Referring to FIG. 1, methanogenic petroleum biodegradation in oil reservoirs proceeds primarily through syntrophic fermentation. Such biodegradation first leads to acetate and hydrogen as intermediates that are then utilized by various microorganisms for further biodegradation to methane. Microbes involved in the acetoclastic methanogenesis pathway convert acetate directly to methane ($CH_4$) and carbon dioxide ($CO_2$). Microbes in the syntrophic acetate oxidation pathway proceed to biodegrade acetate to carbon dioxide and hydrogen. The carbon dioxide is then reduced by microbes in the hydrogenotrophic methanogenesis pathway to methane. These microbes may co-exist with those that are adverse to methanogenesis such as sulfate reducing bacteria that metabolize acetate and hydrogen producing hydrogen sulfide ($H_2S$) water and $CO_2$ and methanotrophs that convert methane to various compounds including water and $CO_2$. The latter two are examples of "non-methane producing competing reactions" described above.

The present invention relates to methods for promoting microbial growth and activity that result in a substantial enhancement in the rate of production of methane ($CH_4$) in a subsurface oil reservoir.

The inventors have discovered that such enhancement can be effected by identifying the petroleum components of a reservoir and determining that they are suitable for methanogenesis, selection of nutrients shown to be effective for the particular microbial consortia in the oil reservoir and then enhancing and preferably maximizing the total amount of nutrients available to the microbes such that methane generation is maximized while at the same time employing a concentration of nutrients in the well that is non-lethal to the microbes.

A major factor in activating adequate subsurface organisms to produce methane over a large volume of subsurface reservoir is to deliver nutrient solutions, at a critical nutrient concentration (ConcA) to activate the microrganisms at a commercial rate, to as large a volume of reservoir as possible. The objective then becomes injecting the minimum volume of water containing nutrients at the maximum safe concentration to avoid deactivating any key organisms (ConcH). At high nutrient concentrations below the critical concentration (ConcH), diffusive transport of nutrients into the formation away from high concentrations of injected advected solutions is at a maximum driven by the large concentration gradients and means that maximum reservoir can be accessed with minimal injected water volumes and raise the largest volume of water to ConcA from the smallest volume of injected water with a nutrient concentration at injection of below ConcH. Fluid concentration injected into the well will therefore be between ConcA and ConcH but ideally at a computed concentration dependent on the known diffusivity of the reservoir medium.

As a starting point, a determination is made of the petroleum components and the endogenous microbes present in the reservoir. Such factors are critical as each reservoir or oil field contains a unique mixture of petroleum components and microbes. Accordingly, the type of petroleum components and microbes present will dictate the nutrients and/or inhibitors which are to be used for that reservoir. Assays for determining the microbes present are known in the art including laboratory incubations of reservoir samples, culturing and culture independent analysis. Likewise, the mixture of hydrocarbons in the reservoir can be determined by conventional analytical means. In one embodiment, a single sample of hydrocarbons is used to determine the hydrocarbons present. In another, multiple samples are used to provide for a higher degree of certainty regarding the hydrocarbon components.

Nutrients and/or inhibitors for the microbes again can be determined based on the microbe type or by laboratory incubations under different conditions.

The selection of the appropriate nutrient(s) and/or inhibitor (s) as well as the total injected amount, rates of injection and injection points is then based on the size of the reservoir, the reservoir properties such as permeability and porosity and the amount and type of petroleum components present as well as the endogenous microbes and the presence of any non-nutrients. As to the size of the reservoir, determination of the field size, the water present, the concentration of nutrients and non-nutrients (e.g., salinity) already in the reservori are well within the skill of the art.

The amount of nutrient (and/or inhibitors) added (injected) into the reservoir is conducted in an iterative process wherein a first injection of nutrients is conducted and after diffusion and equilibration, the concentration of nutrients is determined. Second and subsequent injections, if necessary, can be included until the desired concentration of nutrients is reached.

Optionally, the reservoir can be tested after injection and preferably after equilibration to confirm the concentration of each nutrient and/or inhibitor. Additionally, the reservoir can be retested periodically during methanogenesis to determine if additional nutrient and/inhibitor should be added.

In one embodiment, each of the injections is made through a well head or a plurality of well heads. Such well heads are conventional well heads having access to the subsurface reservoir. The well head(s) for injection can be the same well head(s) for methane recovery. Alternatively, the well head(s) for methane recovery can be one or more well heads specifically dedicated to methane recovery.

In another embodiment, the phosphate ion concentrations for use in combination with the ammonium ions are chosen such that the molar ratio of nitrogen to phosphorus is approximately 10:1. Higher concentrations of phosphorus may be employed including nitrogen to phosphorus ratios of 9:1, 8:1, 7:1, and 6:1. The appropriate phosphorus concentration relative to the nitrogen concentration may be dependent on the particular phosphate reagent that is used and on the nature of the subsurface reservoir. In general the type and amount of phosphate chosen will minimize any precipitation of solids that is typically seen at higher phosphate concentrations.

In one embodiment, the nitrogen is provided by $NH_4Cl$. Other sources of nitrogen include ammonium phosphate.

In one embodiment, the phosphate ion is provided by $KH_2PO_4$. Other sources of phosphate ions for use in the present methods include $KH_2PO_4$, $NaH_2PO_4$, $Na_2HPO_4$, and $H_3PO_4$ in anhydrous or hydrous form. The phosphate ion ($PO_4^{-3}$) is preferably present in an amount of from 700 to 1400 ppm.

In one preferred embodiment, the injected stimulants comprise ammonium, phosphate, nickel, and cobalt ions. It is understood, of course, that type and amount of the injected stimulants will be based on the presence and amount of stimulants already present in the reservoir.

In still other embodiments, one or more buffers are injected into the reservoir. Suitable buffers include carbonates (such as sodium carbonate, sodium bicarbonate, potassium carbonate, potassium bicarbonate) and alkali and alkaline earth hydroxides (such as LiOH, NaOH, KOH, $Cs_2OH$, $Mg(OH)_2$, and $Ca(OH)_2$). In one aspect, the buffer is $NaHCO_3$. The amount of buffer to be added is dependent on the salinity and pH of the reservoir, which can vary from reservoir to reservoir.

In still other embodiments, one or more complexing agents are injected into the reservoir. Such agents include nitrilotriacetic acid. The complexing agents can be used to bind to the stimulants to prevent precipitation and aid in stabilizing the stimulant mixture, can act as inhibitors by binding to metals detrimental to methanogenesis, or act as a source of carbon or nitrogen for microbes to further facilitate biodegradation of oil and methanogenesis, or act as complexing agents to accelerate natural uptake of key nutrient elements from the host reservoir rock.

In yet other embodiments, one or more inhibitors that minimize microbial activity that slow or are detrimental to methanogenesis may be used. Inhibitors include those that inhibit the activity of iron-reducing, nitrate-reducing, or sulphate-reducing bacteria. Specific inhibitors include sodium molybdate ($Na_2MoO_4$) and hydrates of sodium molybdate for inhibiting sulfate reducers, and sodium chlorate ($NaClO_3$) for inhibiting nitrate reducers. Concentrations of sodium molybdate and sodium chlorate of about 20 mM are contemplated as suitable for use in this invention.

The stimulants (ammonium and phosphate ions, minerals, etc.) inhibitors, buffers, and other agents may be combined together in one or more aqueous formulations. In one aspect, the ammonium and phosphate ions are contained in a single formulation. Salts such as NaCl and $CaCl_2$ may also be included in the formulations. The formulations may also be sparged with $N_2$ that will remove oxygen. In some aspects the water used in the formulations is the natural formation water from the reservoir.

In one embodiment, the total salinity of the injected solutions being added to the reservoir will have a salinity similar to that of the reservoir. The salinity of the solutions may be adjusted by modifying the amount of added salts such as NaCl and $CaCl_2$ or other major ions present in the formation water naturally.

Without being bound by theory, the formulation is believed to promote growth of microbes in the syntrophic fermentation, acetoclastic methanogenesis, syntrophic acetate oxidation, and hydrogenotrophic pathways shown in FIG. 1. Microbes involved in methanogenic hydrocarbon degradation include methanogens from the Methanomicrobiales (*Methanocalculus* spp., *Methanogenium* spp., *Methanoculleus* spp.), Methanosarcinales and anaerobic hydrocarbon fermenting bacteria such as *Smithella* spp., *Syntrophus* spp., *Syntrophobacter* spp., *Syntrophomonas* spp., and *Marinobacter* spp.

In one embodiment of the methods, the step of identifying reservoirs having one or more of above features are provided.

An analysis of the reservoir's environment can provide information that can be used to determine suitable microbial growth stimulants or in situ environmental conditions for microbial activity. The analysis can include determining the reservoir's temperature and pressure, which can be obtained in any suitable manner. While many reservoirs contain biodegraded oils, not all reservoirs contain currently active microbial populations. In one implementation, the analysis is to identify a zone in a reservoir that includes relevant active organisms biodegrading reactive petroleum components that can be accelerated to recover economic levels of methane through petroleum biodegradation.

To determine the environment in the reservoir, a geochemical analysis can be made of one or more fluids of the reservoir, such as formation water and petroleum, and/or one or more solids of the reservoir, which analyses are familiar to those skilled in the art. The fluid analysis can include measurement of the state values (e.g., temperature and pressure) as well as a geochemical analysis of the formation water, which can include assays for major anions and cations, pH, oxidation potential (Eh), chloride, bicarbonate, sulphate, phosphate, nitrate, ammonium ion, salinity, selenium, molybdenum, cobalt, copper, nickel, and other trace metals contents. The geochemical analysis can identify products that are known to be produced by indigenous microbial activity. For example, the presence of methane, $CO_2$, RNA, DNA, and/or specific carboxylic acids can be indicative of microbial activity. Methane relatively depleted in the carbon 13 isotope is frequently found in oilfields where natural methanogenesis has occurred. In particular, anaerobic hydrocarbon degradation metabolites, such as alkyl and aryl substituted succinates or reduced naphthoic acids, are markers of systems in which the anaerobic degradation of hydrocarbons is taking place. The identification of such markers can be used in determining the presence of active anaerobic petroleum degrading microbial consortia. See, for example, International Patent Application PCT/CA2009/001069 which is incorporated herein by reference in its entirety.

Injecting fluid through a well head into the zone of maximum microbial populations can include injecting fluid into the zone through a first set of one or more well heads, and producing gas from the zone can include producing gas from the zone through a second set of one or more wells. Injecting fluid into the zone can be concurrent with producing gas from the zone or can cease while producing gas from the zone. Injecting fluid into the zone can include injecting fluid into the zone through a first set of one or more wells and producing gas from the zone can include producing gas from the zone through a second set of one or more wells. A soak cycle can be allowed to endure in a region of the zone situated beneath a third set of one or more wells, while injection and production occur from the first and second set of one or more wells. During a later cycle, the first set of one or more wells can be allowed to endure a soak cycle, fluid can be injected into the zone through the second set of one or more wells and gas can be produced from the zone from the third set of one or more wells.

While producing the methane gas, production parameters are monitored including the pressure in the reservoir, gas production flow rate and composition of the produced gas.

Based on the monitored production parameters, injection into and/or production from the zone are controlled to enhance production of biogenerated methane from the zone.

Implementations of the invention can include one or more of the following features. Controlling injection into and/or production from the zone to enhance production of biogenerated methane from the zone can include controlling one or more of the following: an injector well flow rate; a production well flow rate; a composition of the one or more injectants injected into the reservoir; a quantity of the one or more injectants injected into the reservoir; a composition of the gas injected into the reservoir; a quantity of the gas injected into the reservoir; or a duration of injection, soak and production cycles for the reservoir.

Before producing gas from the zone, an increase in reservoir pressure in the zone in response to an increase in biogenerated methane and the injected fluid can be monitored. Based on the reservoir pressure, the zone's gas saturation can be determined. Production of gas from the zone can be commenced when the zone's gas saturation reaches a threshold gas saturation. The threshold gas saturation is based on the critical gas saturation. In some implementations, the threshold gas saturation is in the range of approximately 85% to 95% of the critical gas saturation. In other implementations, the threshold gas saturation is the critical gas saturation.

The injectants can be added to the reservoir together or in separate injection steps. For example, a slug or bank of water carrying one injectant can be followed by a second slug or bank of water carrying a second injectant. Another example may include alternately injecting one water bank followed by a gas injection step. In some implementations, injectants operating as stimulants may be injected at one location to enhance methanogenesis, and injectants operating as inhibitors may be injected at a different location, to prevent or minimize detrimental processes, such as methane oxidation. Injection of gas below a degrading oil column may facilitate circulation of water and nutrients to the microorganisms present.

In some implementations, layered reservoir bioreactors can be used for methane production and to facilitate methane removal. In such a reservoir bioreactor, the biodegrading oil column and/or residual oil zones are vertically segmented and the environment can be controlled, for example, in the following manner: (a) a lower zone of degradation of oil or injected reactive organic substrates can be environmentally modified to produce abundant free gas (e.g., methane and/or carbon dioxide); (b) an upper zone of degradation of oil or injected reactive organic substrates is environmentally modified to produce abundant free methane; and (c) free gas from the lower layer buoyantly moves up through the layered bioreactor and any free methane or methane in aqueous or oil solution partitions into the moving gas phase and is carried to a gas-rich zone for production.

Microorganisms in subterranean reservoirs tend to be most active at environmental boundaries, such as between fermentation zones and methanogenesis zones. Therefore, microorganism activity in a reservoir may be increased by increasing the number of such boundaries, which serve as environmental interfaces. One method for increasing the number of environmental interfaces is to modify the water flood injection rates. Another method is to alternate or vary the injectants into the reservoir to create, in effect, moving environmental fronts. Yet another method involves forming small-scale environmental interfaces by forming petroleum-water emulsions in the reservoir, or by changing the clay chemistry.

This invention is predicated on the discovery that by
a) evaluating the reservoir in terms of its complex components (petroleum components, the methanogenic microbes present, the endogenous stimulants/inhibitors, the pressure and temperature, the salinity of the formation water, etc.), and
b) evaluating the nature and amount of stimulants and/or inhibitors to be added can be made and then injected into the well, preferably at a concentration above the critical concentration to effect enhanced methanogenesis but below a lethal dosing
significant increases in methane production can be achieved.

Preferably, increases in methanogenesis of at least 10,000 or 100,000 fold or more over endogenous methane production can be achieved. For the sake of completeness, endogenous methane production refers to the amount of methane produced over a given period of time without any intervention in the reservoir which is low being typically on the order of $10^{-4}$ kg/m$^2$ of oil water contact area/year.

Further descriptions of methods and systems for gas production from a reservoir are set forth in Canadian Patent Application No. 3,638,451 which is incorporated herein by reference in its entirety.

The following examples are provided to further illustrate certain aspects of the present invention and to aid those of skill in the art in practicing the invention. These examples are not meant to limit the scope of the invention.

EXAMPLES

The following three solutions were prepared and used in the methods of the invention.

Example 1

A 1L aqueous solution of nutrients for reservoir injection was prepared using the following compounds:

| Nutrient | g/liter H$_2$O |
| --- | --- |
| MgCl$_2$ | 0.363543 |
| NH$_4$Cl | 0.066819 |
| KH$_2$PO$_4$ | 0.016991 |
| NaHCO$_3$ | 0.800235 |
| FeSO$_4$ | 0.001012 |

-continued

| Nutrient | g/liter H$_2$O |
|---|---|
| H$_3$BO$_4$ | 2.65 × 10$^{-5}$ |
| MnCl$_2$ | 5.61 × 10$^{-5}$ |
| CoCl$_2$ | 0.000914 |
| NiCl$_2$ | 0.000115 |
| CuCl$_2$ | 1.39 × 10$^{-6}$ |
| ZnSO$_4$ | 7.13 × 10$^{-5}$ |
| Na$_2$MoO$_4$ | 1.97 × 10$^{-5}$ |
| Na$_2$SeO$_3$ | 4.38 × 10$^{-6}$ |
| Na$_2$WO$_4$ | 6.28 × 10$^{-5}$ |
| NaCl | 7 |
| CaCl$_2$ | 0.12 |
| NaH$_2$PO$_4$ | 0.175 |

Example 2

The following solution was prepared with reservoir water from a Western Canadian sandstone heavy oil reservoir:

| Nutrient | per liter H$_2$O |
|---|---|
| NH$_4$Cl | 5.4 g |
| KH$_2$PO$_4$ | 1.376 g |
| Selenite-tungstate Solution | 1 mL |
| Trace Element Solution | 1 mL |

Optionally, 2.5 mM Na$_2$S can be added as a reducing agent/oxygen scavenger if the solution is stored over a prolonged period of time.

The Selenite-tungstate Solution was prepared as a 1 liter aqueous solution using the following compounds:

| Nutrient | per liter H$_2$O |
|---|---|
| NaOH | 400 mg |
| Na$_2$SeO$_3$ × 5 H$_2$O | 6 mg |
| Na$_2$WO$_4$ × 2 H$_2$O | 8 mg |

The Trace Element Solution was prepared as a 1 liter aqueous solution containing the following compounds:

| Nutrient | per liter H$_2$O |
|---|---|
| HCl (25% = 7.7M) | 12.5 ml |
| FeSO$_4$ × 7 H$_2$O | 2100 mg |
| H$_3$BO$_4$ | 30 mg |
| MnCl$_2$ × 4 H$_2$O | 100 mg |
| CoCl$_2$ × 6 H$_2$O | 190 mg |
| NiCl$_2$ × 6 H$_2$O | 24 mg |
| CuCl$_2$ × 2 H$_2$O | 2 mg |
| ZnSO$_4$ × 7 H$_2$O | 144 mg |
| Na$_2$MoO$_4$ × 7 H$_2$O | 36 mg |

Example 3

Figure 2:
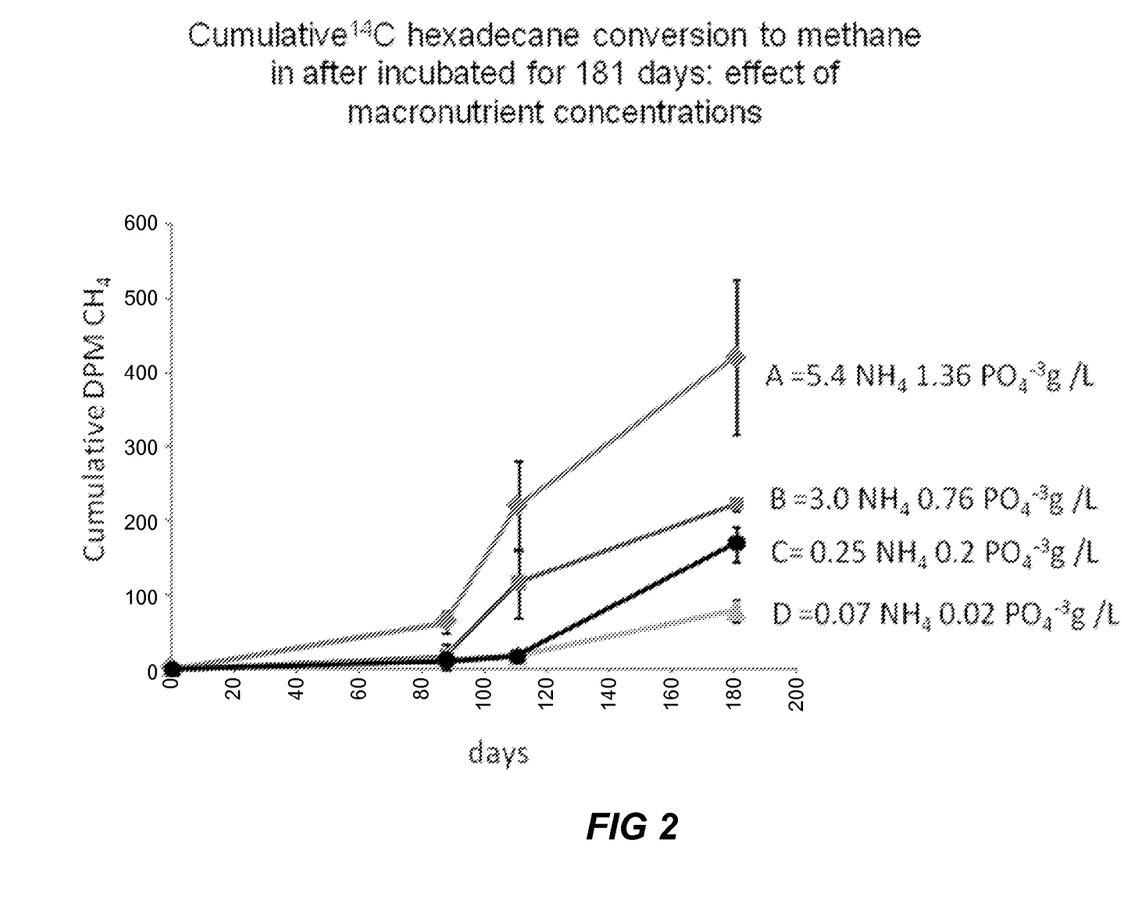
FIG. 2 shows the effect of macronutrient concentration on cumulative $^{14}C$-hexadecane conversion to methane.
Figure 3:
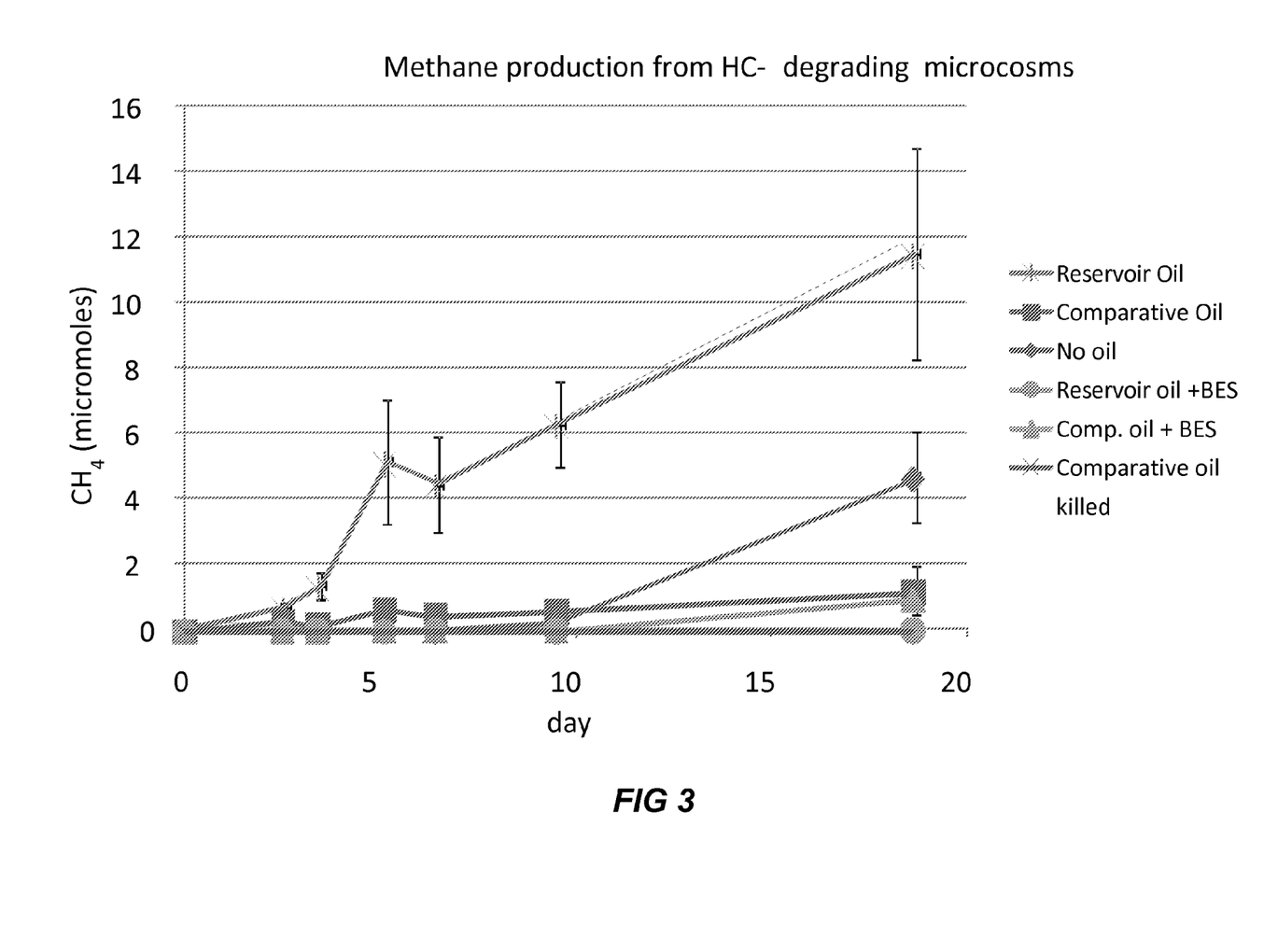
FIG. 3 shows the total amount of methane produced from 125 mg of Reservoir Oil compared to control (no oil), comparative oil, Reservoir Oil containing BES, comparative oil containing BES, and comparative oil heated to kill any endogenous microorganisms.

FIGS. 2 and 3 attached provide an example of significant increases in methanogenesis from the oil of a spent reservoir after injection of nutrients as described below. In particular, the reservoir was selected as it contained methanogenic microorganisms including hydrogenotrophic methanogens (Methanomicrobiales), methylotrophic methanogens (Methanosarcinales) but no, or low numbers of acetoclastic methanogens. In addition the reservoir contained syntrophic methanogenic consortia which converted complex organic carbon (yeast extract) to methane.

A nutrient bolus comprising water and the following nutrients was prepared:

| Nutrient | mg/liter H$_2$O |
|---|---|
| MgCl$_2$ | 1200 |
| CaCl$_2$*2H$_2$O | 150 |
| NH$_4$Cl | 250 |
| KH$_2$PO$_4$ | 200 |
| KCl | 500 |
| NaHCO$_3$ | 2520 |
| FeSO$_4$ | 2.100 |
| H$_3$BO$_4$ | 0.030 |
| MnCl$_2$ | 0.100 |
| CoCl$_2$ | 0.190 |
| NiCl$_2$ | 0.024 |
| CuCl$_2$ | 0.002 |
| ZnSO$_4$ | 0.144 |
| Na$_2$MoO$_4$ | 0.036 |
| Na$_2$SeO$_3$ | 0.006 |
| Na$_2$WO$_4$ | 0.008 |

The concentration of each nutrient was adjusted to show the impact of the concentration on methanogenesis as well as the impact that high concentrations had on dispersion of the nutrients into the formation water which resulted in higher rates of methanogenesis.

Specifically, oil from the reservoir as well as formation waters containing endogenous methanogenic microorganisms were combined in the solution described under example 2 except that the ammonium chloride and potassium phosphate concentrations were varied to give a range of ammonium chloride concentrations from 0.07 to 0.54 g/l and potassium phosphate in the range 0.02 to 1.36 g/l (FIG. 2) $^{14}$C-hexadecane was added and methanogenic degradation of alkanes was followed by monitoring $^{14}$CH$_4$ produced by the degradation of hexadecane over time. Methane production under anaerobic incubations of formation waters with oil was measured. Different levels of nutrients were added to separate samples and the amount of methane produced measured.

Still further, the total amount of methane produced from 125 mg of Reservoir Oil defined above was compared to control (no oil), comparative oil not suitable for methanogenesis, Reservoir Oil containing BES an inhibitor of methanogenesis as a negative control, comparative oil containing BES, and comparative oil heated to kill any endogenous microorganisms. The results of this analysis are set forth in FIG. 3:

As above, Reservoir Oil containing nutrients and methanogenic microbes produced significant amounts of methane. Rates of methane production greater than 0.7 MCF per day were achieved.

All publications and patent applications mentioned in this specification are herein incorporated by reference to the same extent as if each individual publication or patent application was specifically and individually indicated to be incorporated by reference.

Modifications to the invention will be apparent to one of skill in the art given this disclosure. Such modifications and the resulting equivalents to the embodiments and examples described above are intended to be included within the scope of the following claims.

What is claimed is:

1. A method for enhancing methanogenesis in an oil reservoir which method comprises:
   a) identifying a reservoir comprising petroleum components suitable for methanogenesis, formation water and methanogenic microbial consortia wherein said reservoir is endogenously producing a first rate of methane as measured in MCF methane production at a well head per day of less than 0.02 MCF;
b) identifying a set of nutrients based on the formation water and endogenous microbes present in the reservoir wherein said nutrients are selected from endogenous and/or exogenous nutrients;
c) adding a first solution comprising methanogenic nutrients based on the identification set forth in b) above wherein said nutrients comprise at least nitrogen and phosphate ions and further wherein the amount of the nutrients in the first solution is sufficient to enhance the rate of methanogenesis in said reservoir at its final dilution without being lethal to said methanogenic microbial consortia and further wherein the concentration of nutrients in said solution added facilitates dispersion of the nutrients from the first solution into the formation water;
d) maintaining the reservoir under conditions so as to produce a second rate of methane production at the well head of at least 0.7 MCF methane per day.

2. The method of claim 1 which further comprises adding an aqueous solution comprising an inhibitor or mixture of inhibitors wherein the inhibitors are selected from the endogenous and/or exogenous inhibitors and further wherein the amount of the inhibitors in the second aqueous solution is sufficient to maintain a rate of methanogenesis in said reservoir in conjunction with the added nutrients such that the rate of methane production at the well head is at a 0.7 MCF per day and still further wherein the amount of inhibitors added to said reservoir water is non-lethal to said microbes.

3. The method of claim 2, wherein the first solution of nutrients and the aqueous solution of inhibitors are in separate solutions.

4. The method of claim 3, wherein phosphorus and/or nitrogen complexing agents are added to either the solution of nutrients and/or inhibitors.

5. The method of claim 2, wherein the first solution of nutrients and the aqueous solution of inhibitors are in the same solution.

6. The method of claim 5, wherein phosphorus and/or nitrogen complexing agents are added to either the solution of nutrients and/or inhibitors.

7. The method of claim 2, wherein phosphorus and/or nitrogen complexing agents are added to either the solution of nutrients and/or inhibitors.

8. The method of claim 1, wherein phosphorus and/or nitrogen complexing agents are added to the first solution of nutrients.

9. The method of claim 1, wherein the nutrients comprise at least ammonium ($NH_4^+$) and phosphate ($PO_4^{3-}$) ions.

10. The method of claim 1, wherein the nutrients are injected into the reservoir in a manner to maximize dispersion of the nutrients throughout the formation water.

11. The method of claim 1, wherein the nutrients do not contain nitrate or sulfate salts.

12. The method of claim 1, wherein each solution is an aqueous solution.

13. The method of claim 1 wherein the identification of a reservoir suitable for methanogenesis comprises assaying the reservoir for methanogenic microorganisms.

14. The method of claim 1 wherein the methane produced is recovered.

15. A method for increasing the rate of methanogenesis in a petroleum reservoir which method comprises:
a) evaluating the petroleum components in the reservoir, methanogenic microbial consortia present, endogenous stimulants/inhibitors, pressure and temperature, and salinity of formation water in the reservoir;
b) evaluating the nature and amount of stimulants and/or inhibitors to be added based on the evaluation in a) above wherein said stimulants and/or inhibitors are selected from the group of endogenous and/or exogenous stimulants and/or inhibitors;
c) injecting through a well head a solution of stimulants to the reservoir in an amount such that their concentration in the reservoir is above the critical concentration to effect enhanced methanogenesis but below a lethal dosing to the methanogenic microbial consortia; and
d) maintaining said reservoir under conditions such that the rate of methanogenesis is increased to the point that methane production at the well head represents at least a 20 MCF incremental increase in methane production at the well head per day prior to the injection of the solution.

16. The method of claim 15, wherein the stimulants and optionally the inhibitors injected into the well are injected in one or more aqueous solutions.

17. The method of claim 16, wherein the aqueous solution (s) are formulated to have approximately the same salinity as the formation water.

18. The method of claim 17, wherein the amount of water employed in the aqueous solution is maintained at no more than 1000% of the smallest amount of water required to dissolve the stimulants and optionally the inhibitors, and further optionally employing a sequestering agent to maximize solubility.

19. The method of claim 16, wherein the amount of water employed in the aqueous solution is maintained at no more than 1000% of the smallest amount of water required to dissolve the stimulants and optionally the inhibitors, and further optionally employing a sequestering agent to maximize solubility.

20. The method of claim 15, wherein the stimulants are injected into the reservoir in a manner to maximize dispersion of the stimulants throughout the formation water.

21. The method of claim 15, wherein the stimulants do not contain nitrate or sulfate salts.

22. The method of claim 15, wherein each solution is an aqueous solution.

23. A method for increasing the rate of methanogenesis in a reservoir which method comprises:
a) evaluating petroleum components in the reservoir, methanogenic microbial consortia present, endogenous stimulants/inhibitors, pressure and temperature, and salinity of formation water in the reservoir;
b) confirming the presence of at least one or more of the microbes that comprise a methanogenic consortium selected from the group consisting of members of the Methanomicrobiales (*Methanocalculus* spp., *Methanogenium* spp., *Methanoculleus* spp.), the Methanosarcinales and anaerobic hydrocarbon fermenting bacteria such as *Syntrophus* spp., *Smithella* spp., *Syntrophobacter* spp., *Syntrophomonas* spp., and *Marinobacter* spp.;
c) evaluating the nature and amount of stimulants to be added based on the evaluation in a) and b) above wherein the stimulants are selected from the group consisting of those that stimulate one or more members of the methanogenic microbial consortium set forth in b) and further wherein said stimulants are either endogenous and/or exogenous stimulants;
d) evaluating the nature and amount of optional inhibitors to be added based on the evaluation in a) and b) above wherein the inhibitors are selected from the group consisting of those that inhibit one or more non-methanogenic pathways and further wherein said inhibitors are either endogenous and/or exogenous inhibitors;
e) injecting a solution of stimulants into the reservoir through a well head such that after injection the total concentration in the reservoir of stimulants is above the critical concentration to effect enhanced methanogenesis but below a lethal dosing for the methanogenic microbial consortia set forth in b) above wherein the amount of solution employed facilitates dispersion of the stimulants from the aqueous solution into the formation water;
f) optionally injecting a solution comprising inhibitors into the reservoir through the well head such that after injection the total concentration in the reservoir of inhibitors is above the critical concentration to effect inhibition of non-methane producing competing reactions but below a lethal dosing for the methanogenic microbes set forth in b) above wherein the amount of solution employed facilitates dispersion of the nutrients into the formation water; and
g) maintaining said reservoir under conditions such that the rate of methanogenesis is increased to the point that methane production at a well head is at least a 20 MCF incremental increase in methane generation at the well head per day prior to the injection of the solution of nutrients and the optional solution of inhibitors.

24. The method of claim 23 wherein the stimulants are injected into the reservoir in a manner to maximize dispersion of the stimulants throughout the formation water.

25. The method of claim 23, wherein the stimulants do not contain nitrate or sulfate salts.

26. The method of claim 23, wherein each solution is an aqueous solution.

* * * * *